United States Patent [19]

Rohr et al.

[11] 4,411,691

[45] Oct. 25, 1983

[54] 1-SUBSTITUTED PHENYL-PYRIDAZONE HERBICIDES

[75] Inventors: Wolfgang Rohr, Mannheim; Hanspeter Hansen, Ludwigshafen; Bruno Wuerzer, Limburgerhof; Heinz-Guenter Ceser, Ludwigshafen, all of Fed. Rep. of Germany

[73] Assignee: BASF Aktiengesellschaft, Fed. Rep. of Germany

[21] Appl. No.: 344,612

[22] Filed: Feb. 1, 1982

Related U.S. Application Data

[63] Continuation of Ser. No. 194,439, Oct. 6, 1980, abandoned, which is a continuation of Ser. No. 7,006, Jan. 26, 1979, abandoned.

[30] Foreign Application Priority Data

Feb. 25, 1978 [DE] Fed. Rep. of Germany ....... 2808193

[51] Int. Cl.$^3$ ................... A01N 43/58; C07D 237/16; C07D 237/14
[52] U.S. Cl. ......................................... 71/92; 544/240
[58] Field of Search ............................ 71/92; 544/240

[56] References Cited

U.S. PATENT DOCUMENTS

| | | | |
|---|---|---|---|
| 3,323,892 | 6/1967 | Reicheneder | 544/240 |
| 3,326,660 | 6/1967 | Reicheneder | 544/240 |
| 3,376,128 | 4/1968 | Reicheneder | 544/240 |
| 3,697,522 | 10/1972 | Reicheneder | 544/240 |
| 4,027,797 | 3/1978 | Fischer et al. | 544/240 |

*Primary Examiner*—Mark L. Berch
*Attorney, Agent, or Firm*—Keil & Witherspoon

[57] ABSTRACT

Substituted pyridazone derivatives having a good herbicidal action, herbicides containing these compounds as active ingredients, and a process for controlling the growth of unwanted plants with these compounds.

2 Claims, No Drawings

1-SUBSTITUTED PHENYL-PYRIDAZONE HERBICIDES

This is a continuation of application Ser. No. 194,439 filed Oct. 6, 1980, abandoned, which is a continuation of Ser. No. 007,006 filed Jan. 26, 1979, abandoned.

The present invention relates to new and valuable pyridazones, herbicides containing these compounds as active ingredients, and a process for controlling the growth of unwanted plants with these compounds.

It has been disclosed to use 1-phenyl-4,5-dimethoxypyridazone-(6), 1-(m-trifluoromethylphenyl)-4,5-dimethoxypyridazone-(6) and 1-(m-tetrafluoroethoxyphenyl)-4-methylamino-5-chloropyridazone-(6) as herbicides (German Laid-Open Application DE-OS No. 2,526,643, Belgian 728,164, and German No. 1,197,676).

We have now found that substituted pyridazones of the formula

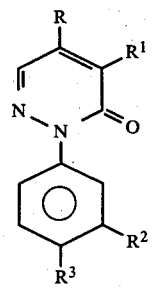

where R and $R^1$ denote lower alkoxy, preferably methoxy, $R^2$ denotes difluoromethyl, fluoro, chloro, or X—$R^4$, X denoting O or S and $R^4$ denoting haloalkyl of 1 to 3 carbon atoms, e.g., —$CHF_2$, —$CF_2$—$CHF_2$, —$CF_2CHF$—$CF_3$, —$CF_2$—$CHFCl$, —$CF_2$—$CHFBr$ or $CF_3$, and $R^3$ denotes hydrogen when $R^2$ is difluoromethyl or X—$R^4$, or fluoro when $R^2$ is fluoro or chloro, have a good herbicidal action.

The new compounds may be prepared by reacting 4,5-dihalo- or 4-alkoxy-5-halopyridazones of the formula

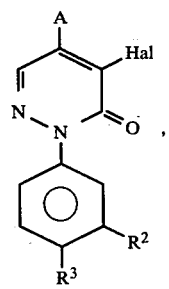

where A denotes halogen (Cl, Br) or alkoxy (methoxy) and Hal denotes halogen (Cl, Br) and $R^2$ and $R^3$ have the above meanings, with an alcoholate of the formula R—R or $R^1$—B, R and $R^1$ having the above meanings and B denoting Na or K, in the presence of an organic liquid.

The 4-alkoxy-5-halopyridazones and 4,5-dihalopyridazones required as starting products are either known or can be obtained in analogy to the processes disclosed in German No. 1,245,207, German No. 1,210,241 and German Laid-Open Application DE-OS No. 2,526,643; for instance, substituted hydrazines are prepared in conventional manner by reduction from the corresponding diazonium salt and are reacted, with or without being isolated as salts, with a 3-formyl-2,3-dihaloacrylic acid in known manner to give the corresponding pyridazone.

Purer products are obtained when the substituted hydrazines are isolated as salts, e.g., hydrochlorides, before the reaction to give the corresponding pyridazone.

When the 4,5-dialkoxypyridazones are prepared by reaction with an alcoholate, there are used for example 2 moles of alcoholate per mole of pyridazone when 4,5-dihalopyridazones are employed, and for example 1 mole of alcohoalte per mole of pyridazone when 4-alkoxy-5-halopyridazones are employed.

Suitable organic solvents are those which are inert to alcoholates between 100° and 160° C., e.g., toluene or xylene. The reaction may be carried out at from 100° to 160° C.

The intermediates have the following physical data:

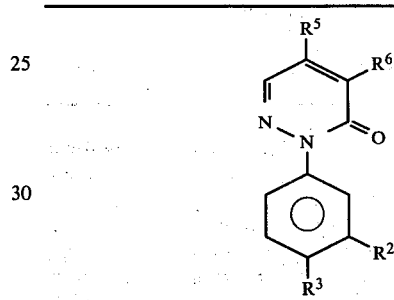

| $R^5$ | $R^6$ | $R^2$ | $R^3$ | m.p. (°C.) |
|---|---|---|---|---|
| Cl | Cl | F | F | 196–197 |
| Cl | Cl | —$CHF_2$ | H | 118–119 |
| Br | Br | O—$CF_2$—CHF—$CF_3$ | H | 72–74 |
| Cl | Cl | Cl | F | 200–202 |
| $CH_3O$ | Cl | —$SCF_3$ | H | 129–131 |
| Cl | Cl | $OCF_2$—$CHF_2$ | H | 74–75 |
| Cl | Cl | O—$CHF_2$ | H | 143–144 |
| Br | Br | O—$CF_2$—CHFCl | H | 72–74 |
| Br | Br | $OCF_3$ | H | 86–88 |
| Cl | Cl | $OCF_2$—CHFBr | H | 67–68 |

EXAMPLE 1

7.2 parts (by weight) of 30% (by weight) sodium methylate solution is concentrated to dryness in vacuo and the residue is slurried in 250 parts of toluene. 10.8 parts of 1-(3-trifluoromethylthiophenyl)-4-methoxy-5-chloropyridazone-6 is added and the suspension is refluxed for 2 hours. After filtration has been carried out, the toluene is evaporated in vacuo. The residue is recrystallized from isopropanol. There is obtained 5.9 parts of 1-(3-trifluoromethylthiophenyl)-4,5-dimethoxypyridazone-6; m.p.: 93°–95° C.

EXAMPLE 2

39.6 parts of 30% sodium methylate solution is evaporated to dryness in vacuo and the residue is slurried in 500 parts of toluene. 36.6 parts of 1-(3-difluoromethoxyphenyl)-4,5-dichloropyridazone-6 is added and the whole refluxed for 2 hours. After filtration has been carried out, the toluene is evaporated in vacuo.

Yield: 28 parts of 1-(3-difluoromethoxyphenyl)-4,5-dimethoxypyridazone-6.

Melting point: 48°-50° C., after chromatography on SiO₂ using a 7:3 mixture of toluene and acetone.

The following compounds are obtained analogously:

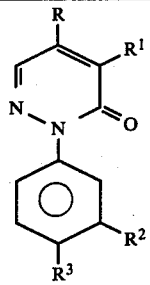

| R | R¹ | R² | R³ | m.p. (°C.) | $n_D^{23}$ |
|---|---|---|---|---|---|
| CH₃O | CH₃O | F | F | 136-138 | |
| CH₃O | CH₃O | —OCF₂—CHF₂ | H | 81-83 | |
| CH₃O | CH₃O | —CHF₂ | H | 52-55 | |
| CH₃O | CH₃O | —O—CF₂—CHF—CF₃ | H | 58-60 | |
| CH₃O | CH₃O | Cl | F | 148-149 | |
| CH₃O | CH₃O | —OCF₃ | H | 84-85 | |
| CH₃O | CH₃O | —OCF₂—CHFCl | H | 64-65 | |
| C₂H₅O | C₂H₅O | —OCF₂—CHF₂ | H | | 1.5177 |
| CH₃O | CH₃O | —OCF₂—CHFBr | H | 68-69 | |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or tering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, talc, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The new herbicidal pyridazones according to the invention may be mixed and applied with numerous representatives of other herbicidal or growth-regulating active ingredient groups. Examples of suitable mixture components are anilides, diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc. Such combinations broaden the spectrum of action, and synergistic effects are at times achieved. A number of active ingredients which together with the new compounds give mixtures useful for various application are as are listed below by way of example.

| R | R¹ | R² |
|---|---|---|
| ⟨phenyl⟩— | NH₂ | Cl |
| ⟨phenyl⟩— | NH₂ | Br |
| ⟨H-phenyl⟩— | NH₂ | Cl |
| ⟨phenyl⟩-CF₃ | —N(CH₃)₂ | Cl |

-continued

| | | | |
|---|---|---|---|
| 3-CF₃-C₆H₄- | —NHCH₃ | Cl | |
| 3-(HCF₂CF₂O)-C₆H₄- | —NHCH₃ | Cl | |
| C₆H₅- | —N(CH₃)₂ | Cl | |

Structure:

R²-, R³-substituted benzene with C(=O)—N(R¹)—SO₂—N(R)— ring

| R | R¹ | R² | R³ | |
|---|---|---|---|---|
| H | i-C₃H₇ | H | H | or salts of this compound |
| H | i-C₃H₇ | H | CH₃ | or salts of this compound |
| —CH₂—OCH₃ | i-C₃H₇ | H | H | |

Pyrido-fused structure: N—CH(CH₃)₂, SO₂, NH — or salts of this compound

Structure: 2,6-dinitroaniline with R¹, R, R², N(R³)(R⁴)

| R | R¹ | R² | R³ | R⁴ |
|---|---|---|---|---|
| H | F₃C | H | C₂H₅ | C₄H₉ |
| H | F₃C | H | n-C₃H₇ | n-C₃H₇ |
| H | F₃C | H | —CH₂—CH₂Cl | n-C₃H₇ |
| H | SO₂NH₂ | H | n-C₃H₇ | n-C₃H₇ |
| H | F₃C | H | n-C₃H₇ | —CH₂-cyclopropyl |
| H₃C | H₃C | H | H | —CH(C₂H₅)₂ |
| H | F₃C | NH₂ | n-C₃H₇ | n-C₃H₇ |
| H | H₃C | H | n-C₃H₇ | n-C₃H₇ |

Structure: R¹-N(R)-C(=O)-O-R²

| R | R¹ | R² |
|---|---|---|
| C₆H₅- | H | i-C₃H₇ |

-continued

| | | |
|---|---|---|
| 3-Cl-C₆H₄- | H | —CH(CH₃)C≡CH |
| 3-Cl-C₆H₄- | H | —CH₂—C≡C—CH₂Cl |
| 3-Cl-C₆H₄- | H | i-C₃H₇ |
| C₆H₅- | H | —CH(CH₃)—CO—NH—C₂H₅ |
| C₆H₅- | H | —N=C(CH₃)₂ |

Structure: R-N(R¹)-C(=O)-O-C₆H₄-NH-C(=O)-O-R²

| R | R¹ | R² |
|---|---|---|
| 3-CH₃-C₆H₄- | H | CH₃ |
| C₆H₅- | H | C₂H₅ |
| C₆H₅- | CH₃ | CH₃ |
| 3,4-F₂-C₆H₃- | H | C₂H₅ |
| 3-Cl-4-F-C₆H₃- | H | C₂H₅ |

Structure: R¹-N(R)-C(=O)-S-R²

| R | R¹ | R² |
|---|---|---|
| i-C₃H₇ | i-C₃H₇ | —CH₂—CCl=CCl₂ |
| i-C₃H₇ | i-C₃H₇ | —CH₂—CCl=CHCl |
| n-C₃H₇ | n-C₃H₇ | C₂H₅ |
| cyclohexyl | C₂H₅ | C₂H₅ |
| sec.-C₄H₉ | sec.-C₄H₉ | C₂H₅ |
| n-C₃H₇ | n-C₃H₇ | n-C₃H₇ |
| i-C₄H₉ | i-C₄H₉ | C₂H₅ |

-continued

| | | |
|---|---|---|
| bicycloheptyl-CH | C₂H₅ | C₂H₅ |
| i-C₃H₇ | i-C₃H₇ | —CH₂— (3-methyl-isoxazol-5-yl) |
| i-C₃H₇ | i-C₃H₇ | —CH₂— (3-ethyl-isoxazol-5-yl) |

$$\underset{H_3C\ CH_3}{\underset{|}{(CH_3)_2CHCH_2-C-}}N-\underset{O}{\underset{\|}{C}}-S-R$$

| R |
|---|
| —CH₂—CCl=CHCl |
| —CH₂—CCl=CCl₂ |

$$R-\underset{Y}{\overset{X}{\underset{|}{C}}}-\underset{O}{\underset{\|}{C}}-O-R^1$$

| R | X | Y | R¹ |
|---|---|---|---|
| CH₃ | Cl | Cl | Na |
| 4-Cl-C₆H₄-CH₂ | Cl | H | CH₃ |
| C₆H₅-C(O)-NH-O- | H | H | H, or salts of this compound |
| Cl | Cl | Cl | Na |
| 2,4-Cl₂-C₆H₃-O-C₆H₄-O- | H | CH₃ | CH₃ |
| C₆H₅-C(O)-N(CH₃)-(3,4-Cl₂-C₆H₃)- | H | CH₃ | C₂H₅ |
| C₂H₅ | Cl | Cl | Na |
| C₆H₅-C(O)-N(CH₃)-(3-Cl-4-F-C₆H₃)- | H | CH₃ | i-C₃H₇ |
| C₆H₅-C(O)-N(CH₃)-(3-Cl-4-F-C₆H₃)- | H | CH₃ | CH₃ |

-continued

| | | | |
|---|---|---|---|
| 4-Cl-C₆H₄-O-C₆H₄-O- | H | CH₃ | —CH₂—CH(CH₃)₂ |
| 3,5-Cl₂-pyridyl-2-O-C₆H₄-O- | H | CH₃ | Na |
| 4-F₃C-C₆H₄-O-C₆H₄-O- | H | CH₃ | CH₃ |

$$\begin{array}{c}X\\|\\\underset{R}{N}\overset{N}{\underset{\underset{R^3}{|}}{\diagdown}}\underset{N}{\diagup}\overset{N}{\underset{\underset{R^2}{|}}{\diagdown}}\end{array}$$

| R | R¹ | R² | R³ | X |
|---|---|---|---|---|
| H | tert.-C₄H₉ | H | C₂H₅ | SCH₃ |
| H | i-C₃H₇ | H | i-C₃H₇ | SCH₃ |
| H | i-C₃H₇ | H | C₂H₅ | SCH₃ |
| H | CH₃ | H | i-C₃H₇ | SCH₃ |
| H | i-C₃H₇ | H | C₂H₅ | Cl |
| H | i-C₃H₇ | H | cyclopropyl | Cl |
| H | C₂H₅ | H | C₂H₅ | Cl |
| H | C₂H₅ | H | —C(CH₃)₂—CN | Cl |
| H | i-C₃H₇ | H | i-C₃H₇ | Cl |
| H | i-C₃H₇ | H | i-C₃H₇ | OCH₃ |
| H | NC—C(CH₃)₂— | H | cyclopropyl | Cl |
| H | C₂H₅ | H | —CH(CH₃)—CH₂—OCH₃ | Cl |
| H | C₂H₅ | H | —CH(CH₃)—C≡CH | Cl |

$$\underset{R}{\overset{R^1}{\underset{|}{N}}}-\underset{O}{\underset{\|}{C}}-R^2$$

| R | R¹ | R² |
|---|---|---|
| CH₃ | CH₃ | —CH(C₆H₅)₂ |
| 1-naphthyl- | H | 2-COOH-C₆H₄- |
| C₂H₅ | C₂H₅ | —CH(CH₃)—O-naphthyl |
| HC≡C—C(CH₃)₂— | H | 3,5-Cl₂-C₆H₃- |

-continued
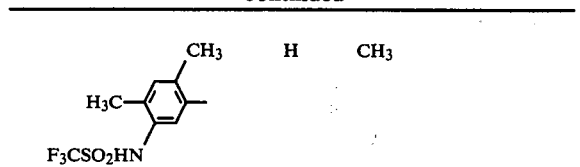
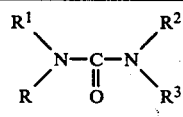
| R | R¹ | R² | R³ |
|---|---|---|---|
| 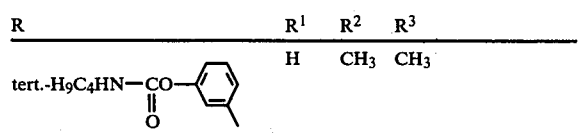 | H | CH₃ | CH₃ |
| 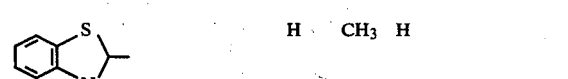 | H | CH₃ | H |
|  | H | CH₃ | CH₃ |
| 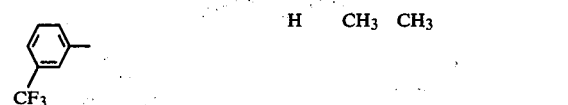 | H | CH₃ | CH₃ |
| 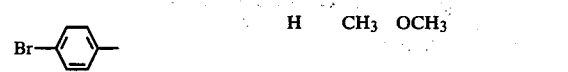 | H | CH₃ | OCH₃ |
| 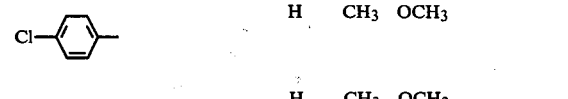 | H | CH₃ | OCH₃ |
|  | H | CH₃ | OCH₃ |
|  | H | CH₃ | OCH₃ |
|  | H | CH₃ | CH₃ |
|  | H | —CH₂—CH(CH₃)₂ | |
| 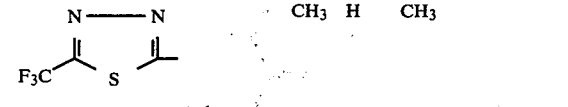 | CH₃ | H | CH₃ |
|  | H | CH₃ | CH₃ |
-continued
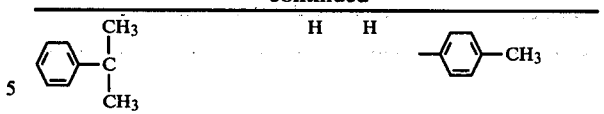
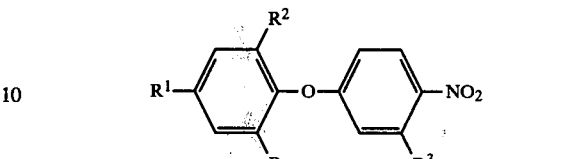
| R | R¹ | R² | R³ |
|---|---|---|---|
| NO₂ | CF₃ | H | H |
| Cl | CF₃ | H | COOH, or salts or esters of this compound |
| Cl | Cl | H | —C(=O)—OCH₃ |
| H | CF₃ | Cl | —OC₂H₅ |
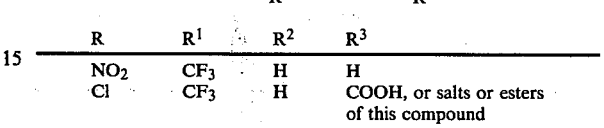
| R | R¹ | R² |
|---|---|---|
| tert.-C₄H₉ | NH₂ | SCH₃ |
| 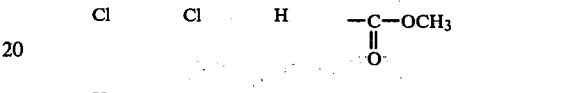 | NH₂ | CH₃ |
| tert.-C₄H₉ | —N=CH—CH(CH₃)CH₃ | SCH₃ |
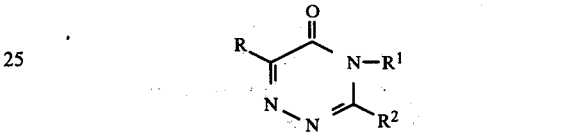
| R | R¹ | R² | R³ |
|---|---|---|---|
| H | CH₃ | Br | —CH(CH₃)—C₂H₅ |
| H | CH₃ | Cl | tert.-C₄H₉ |
| H | CH₃ | Cl | 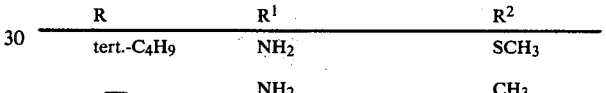 |
| H | —(CH₂)₃— | | 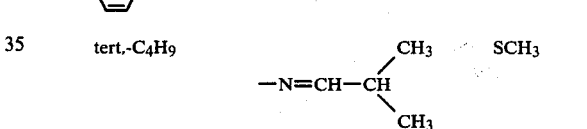 |
| H | CH₃ | Br | C₃H₇i |
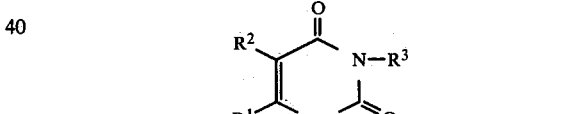

-continued
| R | R¹ |
|---|---|
| CH₃ | C₂H₅ |
| 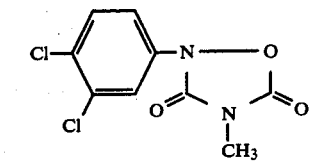 | C₂H₅ |
| 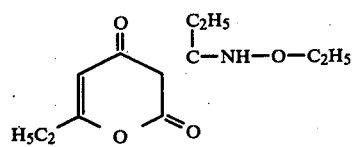 | C₂H₅ |
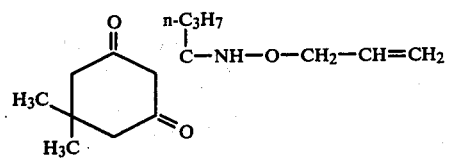
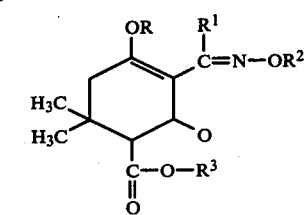
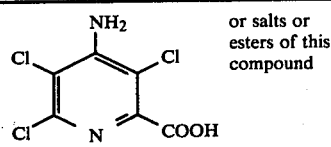
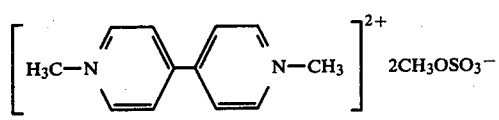
| R | R¹ | R² | R³ |
|---|---|---|---|
| H | n-C₃H₇ | —CH₂—CH=CH₂ | CH₃ |
| Na | n-C₃H₇ | —CH₂—CH=CH₂ | CH₃ |
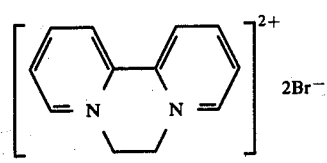 or salts or esters of this compound
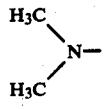
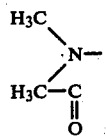
-continued
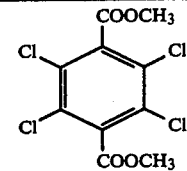
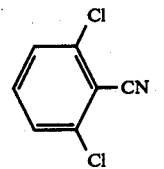
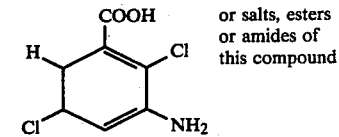 or salts, esters or amides of this compound
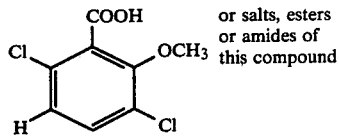 or salts, esters or amides of this compound
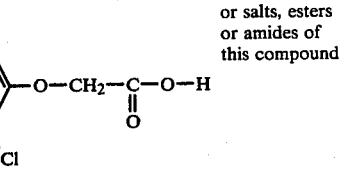 or salts, esters or amides of this compound
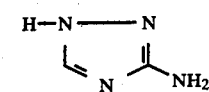
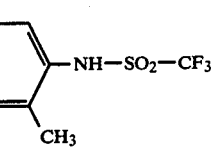
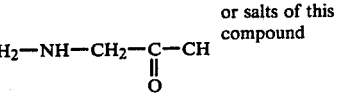 or salts of this compound
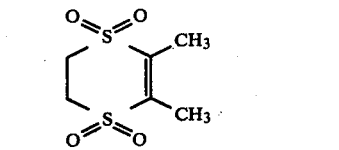
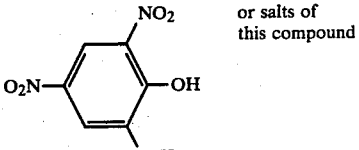 or salts of this compound
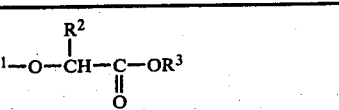

-continued

| R¹ | R² | R³ | |
|---|---|---|---|
| 2,4-dichlorophenyl | H | H | salts, esters, amides |
| 2,4-dichlorophenyl | CH₃ | H | " |
| 4-chloro-2-methylphenyl | H | H | " |
| 4-chloro-2-methylphenyl | CH₃ | H | " |
| 2,4,5-trichlorophenyl | H | H | " |
| 2,4,5-trichlorophenyl | CH₃ | H | " |

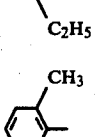

| R¹ | R² | R³ |
|---|---|---|
| $-\underset{\underset{O}{\|}}{C}-CH_3$ | sec.C₄H₉ | H |
| $-\underset{\underset{O}{\|}}{C}-CH_3$ | tert.C₄H₉ | H |
| $-\underset{\underset{O}{\|}}{C}-CH_3$ | tert.C₄H₉ | CH₃ |
| H | CH₃ | H salts and esters |
| H | sec.C₄H₉ | H salts and esters |
| H | tert.C₄H₉ | H salts and esters |
| H | tert.C₄H₉ | CH₃ salts and esters |

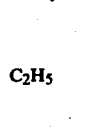

| R¹ | R² | R³ |
|---|---|---|
| phenyl | $-\underset{\underset{C\equiv CH}{\|}}{CH}-CH_3$ | CH₂Cl |
| 2-methyl-3-ethylphenyl | $-\underset{\underset{OCH_3}{\|}}{CH}-CH_2-OCH_3$ | CH₂Cl |
| 2,6-dimethyl-3-methylphenyl | —CH₂—CH₂OCH₃ | CH₂Cl |
| 2,6-diethylphenyl | —CH₂—OCH₃ | CH₂Cl |
| 2,6-diethylphenyl | $-CH_2-\underset{\underset{O}{\|}}{C}-OC_2H_5$ | CH₂Cl |
| 2,6-diethylphenyl | —CH₂—O—C₄H₉n | CH₂Cl |
| 2,6-dimethylphenyl | dioxolanylmethyl | CH₂Cl |
| 3,4-dichlorophenyl | H | cyclopropyl |
| 3,4-dichlorophenyl | H | C₂H₅ |
| 4-chlorophenyl | H | —C(CH₃)₂—C₃H₇ |
| 3-methyl-5-(trifluoromethylsulfonylamino)phenyl | H | CH₃ |

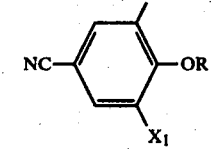

| X | X₁ | R |
|---|---|---|
| Br | Br | H and salts |
| I | I | H and salts |
| Br | Br | $-\underset{\underset{O}{\|}}{C}-(CH_2)_6-CH_3$ |

-continued

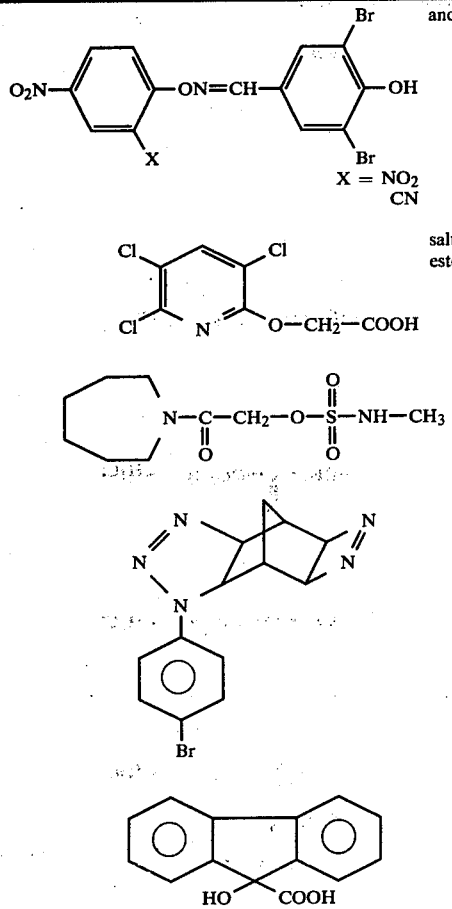

EXAMPLE 3

Herbicidal action of the new compounds

The following experiments demonstrate the influence of various compounds according to the invention on the germination and growth of unwanted and crop plants. The series of experiments were carried out in the greenhouse and in the open.

I. Greenhouse exeriments

Plastic flowerpots having a volume of 300 cm³ were filled with a loamy sand containing about 1.5% humus. Seeds of the test plants given in Table 1 were sown shallow, and separated according to species. In the preemergence treatment, the active ingredients were then applied immediately to the surface of the soil. The active ingredients were suspended or emulsified in water as the vehicle and sprayed onto the surface of the soil by means of atomizing nozzles. After treatment, the vessels were lightly sprinkler-irrigated to stimulate germination and growth, and to activate the chemical compounds. The vessels were then covered with transparent plastic hoods until the plants had taken root. This cover ensured uniform germination of the test plants, to the extent that this was not impaired by the active ingredient.

For the postemergence treatment, the plants were first grown to a height of from 3 to 10 cm, depending on habit, before being treated. No hoods were placed on the pots. The plants were placed in either cooler (15°–30° C.) or warmer (25°–40° C.) parts of the greenhouse, depending on their temperature requirements. The experiments were run for from 4 to 6 weeks. During this period the plants were tended and their reaction to the individual treatments was assessed. The application rate of the compounds examined is given in kg/ha of active ingredient. For assessment, the 0 to 100 scale was used, 0 denoting no damage or normal emergence, and 100 denoting no emergence or complete destruction of at least the visible plant parts.

II. Experiments in the open

The experiments were carried out on small plots in a loamy sand (pH 5 to 6) containing from 1 to 1.5% humus. Treatment was preemergence, and was effected either immediately after sowing or at the latest 3 days later. The crop plants were sown in rows. The weed flora was made up of widely varying species and was natural. The compounds were applied, as an emulsion or suspension in water, with the aid of a motor-driven plot spray. Where no rain fell, sprinkling was carried out to ensure germination and growth of crop plants and weeds. All the experiments were run for several weeks or months. During this period, assessments on the 0 to 100 scale were made at various intervals.

Results

The new compounds exhibit a high degree of herbicidal activity (Tables 2, 3, 4, 5 and 6). Compared with prior art active ingredients, they offer advantages either with regard to their action on unwanted plants or they are much better tolerated by crop plants.

The compounds according to the invention are selective herbicidal active ingredients for the control of unwanted plants in agricultural and horticultural crops and forestry. They may also be used for removing plant growth on non-cropland, e.g., as total weedkillers on railroads, parking lots and in industrial plants. They may further be used for controlling or eliminating the growth of unwanted woody plants in aggregate and other fruit, nuts and grapes. Examples of crop plants are as follows:

| Botanical name | Common name |
|---|---|
| *Allium cepa* | onions |
| *Ananas comosus* | pineapple |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemon |
| *Citrus maxima* | grapefruit |
| *Citrus reticulata* | |
| *Citrus sinensis* | orange trees |
| *Coffea arabica* (*Coffea canephora, Coffea liberica*) | coffee plants |
| *Cucumis melo* | melons |
| *Cucumis sativus* | cucumber |
| *Cynodon dactylon* | Bermudagrass in turf and lawns |
| *Daucus carota* | carrots |
| *Elacis guineensis* | oil palms |
| *Fragaria vesca* | strawberries |
| *Glycine max* | soybeans |
| *Gossypium hirsutum* | cotton |

-continued

| Botanical name | Common name |
|---|---|
| (Gossypium arboreum | |
| Gossypium herbaceum | |
| Gossypium vitifolium) | |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potato |
| Juglans regia | walnut trees |
| Lactuca sativa | lettuce |
| Lens culinaris | lentils |
| Linum usitatissimum | flax |
| Lycopersicon lycopersicum | tomato |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir |
| Pinus spp. | pine trees |
| Pisum sativum | English peas |
| Prunus avium | cherry trees |
| Prunus domestica | plum trees |
| Prunus dulcia | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | Sesami |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberry |
| Vaccinium vitis-idaea | cranberry |
| Vicia faba | tick beans |
| Vigna sinensis (V. unguiculata) | cow peas |
| Vitis vinifera | grapes |

-continued

| Botanical name | Common name |
|---|---|
| Zea mays | Indian corn, sweet corn, maize |

In the tables, pre- and postemergence use are documented. In addition to surface aplication, the agents may of course also be incorporated into the soil either before or after crop plants are sown, or after the crop plants have emerged.

Special applications such as post-directed or lay-by treatment are also possible. In this case, the spray is directed in such a manner that the leaves of sensitive crop plants are not touched; the agents are sprayed onto the soil beneath the crop plants, or the unwanted plants growing there.

In view of the wide variety of application methods, the agents according to the invention, or compositions containing them, may be used not only in the crop plants in the above tables, but also in a further large number of crop plants for eliminating unwanted plants. The application rates may vary from 0.1 to 15 kg/ha and more, depending on the object to be achieved.

TABLE 1

List of test plants

| Botanical name | Abbreviation in tables | Common name |
|---|---|---|
| Abutilon theophrasti | Abutilon theo. | velvet leaf |
| Alopecurus myosuroides | Alepec. myos. | slender foxtail |
| Amaranthus retroflexus | Amar. retr. | redroot pigweed |
| Avena fatua | Avena fat. | wild oats |
| Chenopodium album | Chenop. alb. | lambsquarters (goosefoot) |
| Chrysanthemum segetum | Chrys. seg. | corn marigold |
| Ipomoea spp. | Ipom. spp. | morningglory |
| Datura stramonium | Datura stram. | jimsonweed |
| Echinochloa crus galli | Echin. c.g. | barnyardgrass |
| Euphorbia geniculata | Euph. gen. | South American member of the spurge family |
| Galium aparine | Galium apar. | catchweed bedstraw |
| Glycine max | Glyc. max | soybeans |
| Gossypoum hirsutum | Gossyp. hirs. | cotton |
| Matricaria spp. | Matric. spp. | chamomile |
| Oryza sativa | Oryza sat. | rice |
| Polygonum persicaria | Polyg. pers. | ladysthumb |
| Portulaca oleracea | Port. oler. | purslane |
| Sida spinosa | Sida pin. | teaweed (prickly sida) |
| Sinapis alba | — | white mustard |
| Solanum nigrum | Solan. nigr. | black nightshade |
| Stellaria media | — | chickweed |
| Veronica spp. | — | speedwell |

TABLE 2

Herbicidal action and tolerance of active ingredients by crop plants;
preemergence application in the greenhouse Basic structure

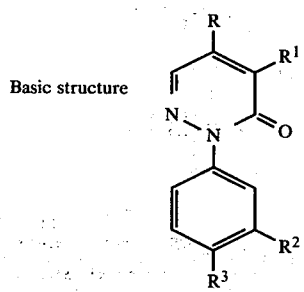

| Com- pound | Test plants and % damage | | | | | | |
|---|---|---|---|---|---|---|---|
| | Glyc. | Gossyp. | Oryza | Abutilon | Alopec. | Amaranth. | Chrys. |

TABLE 2-continued
Herbicidal action and tolerance of active ingredients by crop plants; preemergence application in the greenhouse Basic structure 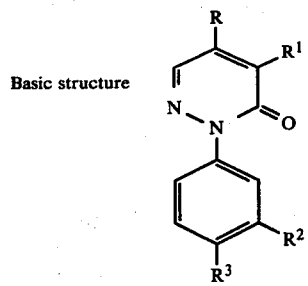

| no. | R | R¹ | R² | R³ | kg/ha | max | hirs. | sat. | theo. | myos. | retr. | seg. |
|---|---|---|---|---|---|---|---|---|---|---|---|---|
| 1 | OCH₃ | OCH₃ | F | F | 1.0 | 0 | — | 10 | — | — | 98 | 90 |
| 2 | OCH₃ | OCH₃ | —CHF₂ | H | 0.5 | 10 | — | — | 100 | 70 | 30 | — |
|  |  |  |  |  | 1.0 | 10 | — | — | 100 | 100 | 100 | — |
| 3 | OCH₃ | OCH₃ | —OCF₂—CHF—CF₃ | H | 0.5 | 15 | 0 | — | 100 | 70 | 100 | — |
|  |  |  |  |  | 1.0 | 55 | 0 | — | 100 | 98 | 100 | — |
|  |  |  |  |  |  |  |  |  | Portulac. |  |  | Euph. gen. |
| 4 | OCH₃ | OCH₃ | —OCHF₂ | H | 0.5 | — | 10 | — | 100 | 90 | 40 | 100 |
|  |  |  |  |  | 1.0 | — | 20 | — | 100 | 95 | 75 | 100 |
|  |  |  |  |  |  |  |  |  | Abutilon |  |  |  |
| 5 | OCH₃ | OCH₃ | —OCF₂—CHF₂ | H | 0.5 | — | 0 | 10 | 100 | 92 | 98 | 100 |
|  |  |  |  |  | 1.0 | — | 5 | 20 | 100 | 95 | 98 | 100 |
|  |  |  |  |  | 2.0 | — | 10 | 60 | — | 95 | 95 | 100 |
| A prior art | OCH₃ | OCH₃ | H | H | 0.5 | 15 | 40 | 20 | 90 | 52 | 78 | 95 |
|  |  |  |  |  | 1.0 | 15 | 55 | 20 | 100 | 72 | 93 | 100 |

| Compound no. | R | R¹ | R² | R³ | kg/ha | Test plants and % damage |  |  |  |  |  |  |
|---|---|---|---|---|---|---|---|---|---|---|---|---|
|  |  |  |  |  |  | Datura stram. | Ipom. spp. | Matric spp. | Sida spin. | Sinapsis alba | Solan. nigr. | Stellaria media |
| 1 | OCH₃ | OCH₃ | F | F | 1.0 | 80 | — | 100 | 70 | 90 | 98 | — |
| 2 | OCH₃ | OCH₃ | —CHF₂ | H | 0.5 | 95 | 100 | 100 | 100 | — | 100 | 100 |
|  |  |  |  |  | 1.0 | 95 | 100 | 100 | 100 | — | 100 | 100 |
| 3 | OCH₃ | OCH₃ | —OCF₂—CHF—CF₃ | H | 0.5 | 75 | 100 | 100 | 100 | — | 100 | 100 |
|  |  |  |  |  | 1.0 | 95 | 100 | 100 | 100 | — | 100 | 100 |
| 4 | OCH₃ | OCH₃ | —OCHF₂ | H | 0.5 | — | 65 | 100 | 70 | — | 45 | 90 |
|  |  |  |  |  | 1.0 | — | 65 | 100 | 95 | — | 70 | 100 |
|  |  |  |  |  |  |  |  |  |  | Echin. |  |  |
| 5 | OCH₃ | OCH₃ | —OCF₂—CHF₂ | H | 0.5 | 95 | 85 | 100 | 98 | 55 | 98 | 100 |
|  |  |  |  |  | 1.0 | 95 | 90 | 100 | 98 | 80 | 98 | 100 |
|  |  |  |  |  | 2.0 | — | 100 | 100 | 100 | 95 | 95 | 100 |
| A prior art | OCH₃ | OCH₃ | H | H | 0.5 | 89 | 66 | 100 | 53 | 98 | 92 | 94 |
|  |  |  |  |  | 1.0 | 94 | 100 | 100 | 69 | 98 | 98 | 98 |

0 = no damage
100 = plants destroyed

TABLE 3
Herbicidal action and tolerance of new active ingredients by crop plants; preemergence application in the open Basic structure 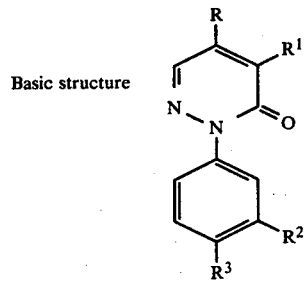

| Compound no. | R | R¹ | R² | R³ | kg/ha | Test plants and % damage |  |  |  |  |
|---|---|---|---|---|---|---|---|---|---|---|
|  |  |  |  |  |  | Gossyp. hirs. | Amar. retr. | Chenop. alb. | Echin. c.g. | Polyg. pers. |
| 5 | OCH₃ | OCH₃ | —OCF₂—CHF₂ | H | 1.0 | 1 | 67 | 84 | 51 | 30 |
|  |  |  |  |  | 2.0 | 11 | 93 | 95 | 78 | 70 |
| A | OCH₃ | OCH₃ | H | H | 1.0 | 20 | 90 | 92 | 37 | 10 |

TABLE 3-continued

Herbicidal action and tolerance of new active ingredients by crop plants; preemergence application in the open

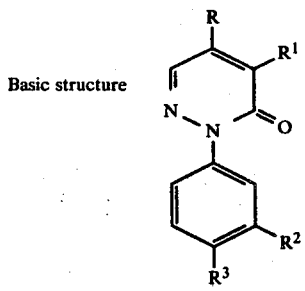

Basic structure

| Compound no. | R | R¹ | R² | R³ | kg/ha | Test plants and % damage | | | | |
|---|---|---|---|---|---|---|---|---|---|---|
| | | | | | | Gossyp. hirs. | Amar. retr. | Chenop. alb. | Echin. c.g. | Polyg. pers. |
| prior art | | | | | 2.0 | 55 | 100 | 99 | 68 | 56 |
| B prior art | −N(H)(CH₃) | Cl | −OCF₂−CHF₂ | H | 1.0 | 19 | 72 | 35 | 34 | 2 |
| | | | | | 2.0 | 36 | 92 | 60 | 58 | 12 |

0 = no damage  
100 = non-emergence, or plants destroyed

TABLE 4

Herbicidal action of new active ingredients; postemergence application in the greenhouse

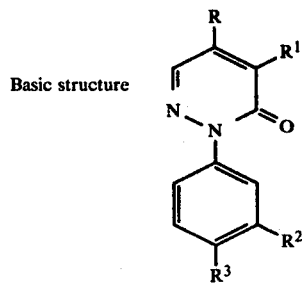

Basic structure

| Compound no. | R | R¹ | R² | R³ | kg/ha | Test plants and % damage | | | | | | | |
|---|---|---|---|---|---|---|---|---|---|---|---|---|---|
| | | | | | | Avena fat. | Echin. c.g. | Amar. retr. | Euph. gen. | Galium agar | Port. oler. | Sida spin. | Veronica spp. |
| 5 | OCH₃ | OCH₃ | −OCF₂−CHF₂ | H | 1.0 | 100 | 98 | 100 | 100 | 95 | 100 | 100 | 100 |
| 3 | OCH₃ | OCH₃ | −OCF₂−CHF−CF₃ | H | 1.0 | — | 100 | 100 | — | 90 | — | 100 | — |
| 4 | OCH₃ | OCH₃ | −OCHF₂ | H | 1.0 | 100 | 85 | 90 | 20 | — | 100 | 100 | 100 |
| 2 | OCH₃ | OCH₃ | −CHF₂ | H | 1.0 | — | 100 | — | — | 80 | — | 60 | — |
| 6 | OCH₃ | OCH₃ | −SCF₃ | H | 1.0 | — | 80 | — | — | 98 | — | — | — |
| A prior art | OCH₃ | OCH₃ | H | H | 1.0 | 80 | 70 | 75 | 22 | 60 | 100 | 80 | 100 |

0 = no damage  
100 = plants destroyed

TABLE 5

Selective herbicidal action of the active ingredients;
preemergence application in the greenhouse Basic structure:

$$\text{pyridazinone with } R, R_1, R_2, R_3 \text{ substituents on phenyl ring}$$

| Compound no | R | $R_1$ | $R_2$ | $R_3$ | kg/ha | Gossypium hirsutum cotton | Abutilon theophrasti | Echinochloa crus galli | Euphorbia geniculata | Ipomoea spp. | Portulaca oleracea | Sesbania exaltata | Setaria faberii | Sida spinosa |
|---|---|---|---|---|---|---|---|---|---|---|---|---|---|---|
| 2 | —OCH$_3$ | OCH$_3$ | —CHF$_2$ | H | 0.25 | 0 | — | 85 | 100 | 75 | 89 | — | 70 | 95 |
|   |          |         |          |   | 0.5  | 10 | 92 | 85 | — | 98 | 89 | 72 | 98 | 100 |
| 3 | —OCH$_3$ | —OCH$_3$ | —OCF$_2$—CHF—CF$_3$ | H | 0.25 | 3 | 88 | 53 | 100 | 72 | 89 | 50 | 65 | 90 |
|   |          |          |                    |   | 0.5  | 3 | 100 | 72 | 100 | 98 | 94 | 87 | 75 | 100 |
| 5 | —OCH$_3$ | —OCH$_3$ | —OCF$_2$—CHF$_2$ | H | 0.25 | 15 | 100 | 92 | 98 | 75 | 90 | 65 | 85 | 100 |
| 6 | —OCH$_3$ | —OCH$_3$ | —SCF$_3$ | H | 0.5 | 10 | 100 | 79 | 100 | 100 | 92 | 90 | 100 | 100 |
| C prior art | —OCH$_3$ | OCH$_3$ | CF$_3$ | H | 0.25 | 15 | 100 | 69 | 68 | 80 | 85 | 50 | 70 | 100 |

TABLE 6

Herbicidal action of the active ingredients; postemergence
application in the greenhouse Basic structure (dihydropyridazinone with phenyl substituent)

| Compound no. | R | $R_1$ | $R_2$ | $R_3$ | Centaurea cyanus | Echinochloa crus galli | Ipomoea spp. | Lolium multiflorum |
|---|---|---|---|---|---|---|---|---|
| 7 | —OCH$_3$ | OCH$_3$ | —O—CF$_2$—CHFCl | H 3.0 | 100 | 100 | 100 | 100 |
| 8 | —OCH$_3$ | OCH$_3$ | —O—CF$_2$—CHFBr | H 3.0 | 100 | 100 | 100 | 100 |
| 9 | —OC$_2$H$_5$ | OC$_2$H$_5$ | —O—CF$_2$—CHF$_2$ | H 3.0 | — | 100 | 70 | 100 |
| 10 | —OCH$_3$ | —OCH$_3$ | —OCF$_3$ | H 3.0 | 100 | 100 | 100 | 100 |

EXAMPLE 4

90 parts by weight of compound 1 is mixed with 10 parts by weight of N-methyl-α-pyrrolidone. A mixture is obtained which is suitable for application in the form of very fine drops.

EXAMPLE 5

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 7

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 9

3 parts by weight of compound 3 is intimately mixed with 97 parts by weight of particulate kaolin. A dust is obtained containing 3% by weight of the active ingredient.

EXAMPLE 10

30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt % of active ingredient.

EXAMPLE 12

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A substituted pyridazone selected from the group consisting of 1-(3-tetrafluoroethoxyphenyl)-4,5-dimethoxypyridazone-6 and 1-(3-monobromotrifluoroethoxyphenyl)-4,5-dimethoxypyridazone.-6

2. A process for combating the growth of unwanted plants wherein the soil or the plants are treated with a substituted pyridazone selected from the group consisting of 1-(3-tetrafluoroethoxyphenyl)-4,5-dimethoxypyridazone-6 and 1-(3-monobromotrifluoroethoxyphenyl)-4,5-dimethoxypyridazone-6.

* * * * *